US006228582B1

(12) United States Patent
Rodier et al.

(10) Patent No.: US 6,228,582 B1
(45) Date of Patent: May 8, 2001

(54) GENETIC POLYMORPHISMS WHICH ARE ASSOCIATED WITH AUTISM SPECTRUM DISORDERS

(75) Inventors: Patricia M Rodier; Jennifer L. Ingram; Denise A. Figlewicz; Susan L. Hyman; Christopher J. Stodgell, all of Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/095,117

(22) Filed: Jun. 10, 1998

Related U.S. Application Data

(60) Provisional application No. 60/049,803, filed on Jun. 17, 1997.

(51) Int. Cl.[7] .............................. C12Q 1/68; C12P 19/34; C07H 21/04
(52) U.S. Cl. ........................... 435/6; 435/91.2; 536/23.1; 536/24.3
(58) Field of Search ..................... 435/6, 91.2; 536/23.1, 536/24.3

(56) References Cited

PUBLICATIONS

Jorde er al., Am. J. Hum. Genet. vol. 49, pp 932–938, 1991.*
Goddard et al., "Mice With Targeted Disruption of *Hoxb–1* Fail to Form the Motor Nucleus of the VIIth Nerve," *Development*, 122:3217–3228 (1996).
Studer et al., "Genetic Interactions Between *Hoxa1* and *Hoxb1* Reveal New Roles in Regulation of Early Hindbrain Patterning," *Development*, 125:1025–1036 (1998).
Gavalas et al., "*Hoxa1* and *Hoxb1* Synergize in Patterning the Hindbrain, Cranial Nerves and Second Pharyngeal Arch," *Development*, 125:1123–1136 (1998).
Thompson et al., "An Evolutionary Conserved Element is Essential for Somite and Adjacent Mesenchymal Expression of The *Hoxa1* Gene," *Development Dynamics*, 211:97–108 (1998).
Spence et al., "Gene Mapping Studies with the Syndrome of Autism," *Behav. Genet.*, 15:1–13 (1985).
Smalley et al., "Autism and Genetics," *Arch. Gen. Psychiat.*, 45:953 961 (1988).
Cook et al., "Evidence of Linkage Between the Serotonin Transporter and Autistic Disorder," *Molec. Psychiat.*, 2:247 –250 (1997).
Klauck et al., "Serotonin Transporter (5–HTT) Gene Variants Associated with Autism?," *Hum. Molec. Genet.*, 6(13):2233 2238 (1997).
Cook et al., "Linkage–Disequilibrium Mapping of Autistic Disorder, With 15q11–13 Markers," *Am. J. Hum. Genet.*, 62:1077–1083 (1998).
Acampora et al., "The Human HOX Gene Family," *Nucleic Acids Res.*, 17(24):10385–10402 (1989).
Hong et al., "Structure and Function of the *HOX A1* Human Homeobox Gene cDNA," *Gene*, 159:209–214 (1995).
Murphy et al., "Expression of the Mouse *Labial*–Like Homeobox–Containing Genes, *Hox* 2.9 and *Hox* 1.6, During Segmentation of the Hindbrain," *Development*, 111;61–74 (1991).

* cited by examiner

*Primary Examiner*—W. Gary Jones
*Assistant Examiner*—Jehanne Souaya
(74) *Attorney, Agent, or Firm*—Nixon Peabody LLP

(57) ABSTRACT

A method is provided for screening subjects for genetic markers associated with autism. The method involves isolating a biological sample from a mammal and then testing for the presence of a mutated gene or a product thereof which is associated with autism. Also disclosed are isolated nucleic acids encoding HoxA1 and HoxB1, both of which have a polymorphism that is associated with autism spectrum disorders.

29 Claims, 2 Drawing Sheets

A C G T

A C G T

GENETIC POLYMORPHISMS WHICH ARE ASSOCIATED WITH AUTISM SPECTRUM DISORDERS

The present application claims the benefit of U.S. Provisional Patent Application Ser. No. 60/049,803, filed Jun. 17, 1997.

The subject matter of this application was made with support from the United States Government under Grants No. RO1AA08666, RO1 NS 24287, RO1HD34295, RO1HD34969, and 2P30 ES01247 from the National Institutes of Health and Grant No. R824758 from the Environmental Protection Agency. The United States Government may retain certain rights.

FIELD OF THE INVENTION

The present invention relates to a method of screening subjects for genetic markers associated with autism. The invention further relates to isolated nucleic acids having polymorphisms associated with autism, the polypeptide products of those nucleic acids, and antibodies specific to the polypeptides produced by the mutated genes.

BACKGROUND OF THE INVENTION

Autism is a behaviorally defined syndrome characterized by impairment of social interaction, deficiency or abnormality of speech development, and limited activities and interest (American Psychiatric Association, 1994). The last category includes such abnormal behaviors as fascination with spinning objects, repetitive stereotypic movements, obsessive interests, and abnormal aversion to change in the environment. Symptoms are present by 30 months of age. The prevalence rate in recent Canadian studies using total ascertainment is over 1/1,000 (Bryson, S. E. et al., *J. Child Psychol. Psychiat.*, 29, 433 (1988)).

Attempts to identify the cause of the disease have been difficult, in part, because the symptoms do not suggest a brain region or system where injury would result in the diagnostic set of behaviors. Further, the nature of the behaviors included in the criteria preclude an animal model of the diagnostic symptoms and make it difficult to relate much of the experimental literature on brain injuries to the symptoms of autism.

Several quantitative changes have been observed in autistic brains at autopsy. An elevation of about 100 g in brain weight has been reported (Bauman, M. L. and Kemper, T. L., *Neurology* 35, 866 (1985)). While attempts to find anatomical changes in the cerebral cortex have been unsuccessful (Williams, R. S. et al., *Arch. Neurol.*, 37, 749 (1980); Coleman P. D., et al., *J. Autism Dev. Disord.*, 15, 245 (1985)), several brains have been found to have elevated neuron packing density in structures of the limbic system (Bauman, M. L. and Kemper, T. L., *Neurology* 35, 866 (1985)), including the amygdala, hippocampus, septal nuclei and mammillary body. Multiple cases in multiple labs have been found to have abnormalities of the cerebellum. A deficiency of Purkinje cell and granule cell number, as well as reduced cell counts in the deep nuclei of the cerebellum and neuron shrinkage in the inferior olive, have been reported (Bauman, M. L. and Kemper, T. L., *Neurology,* 35, 866 (1985); Bauman, M. L. and Kemper, T. L., *Neurology,* 36 (suppl. 1), 190 (1986); Bauman, M. L. and Kemper, T. L., *The Neurobiology of Autism*, Johns Hopkins University Press, 119 (1994); Ritvo, E. R. et al., *Am. J. Psychiat.*, 143, 862 (1986); Kemper, T. L. and Bauman M. L., *Neurobiology of Infantile Autism*, Elsevier Science Publishers, 43 (1992)).

Imaging studies have allowed examination of some anatomical characteristics in living autistic patients, providing larger samples than those available for histologic evaluation. In general, these confirm that the size of the brain in autistic individuals is not reduced and that most regions are also normal in size (Piven, J. et al., *Biol. Psychiat.*, 31, 491 (1992)). Reports of size reductions in the brainstem have been inconsistent (Gaffney, G. R. et al., *Biol. Psychiat.*, 24, 578 (1988); Hsu, M. et al., *Arch. Neurol.* 48, 1160 (1991)), but a new, larger study suggests that the midbrain, pons, and medulla are smaller in autistic cases than in controls (Hashimoto, T. et al., *J. Aut. Dev. Disord.*, 25, 1 (1995)). In light of the histological effects reported for the cerebellum, it is interesting that the one region repeatedly identified as abnormal in imaging studies is the neocerebellar vermis (lobules VI and VII; Gaffney, G. R. et al., *Am. J. Dis. Child.,* 141, 1330 (1987); Courchesne E., et al., *N. Engl. J. Med.*, 318, 1349 (1988); Hashimoto, T. et al., *J. Aut. Dev. Disord.*, 25, 1 (1995)). Not all comparisons have found a difference in neocerebellar size (Piven, J. et al., *Biol. Psychiat.*, 31, 491 (1992); Kleiman, M. D. et al., *Neurology,* 42, 753 (1992)), but a recent reevaluation of positive and negative studies (Courchesne, E. et al, *Neurology,* 44, 214 (1994)) indicates that a few autistic cases have hyperplasia of the neocerebellar vermis, while many have hypoplasia. Small samples of this heterogeneous population could explain disparate results regarding the size of the neocerebellum in autism. The proposal that the cerebellum in autistic cases can be either large or small is reasonable from an embryological standpoint, because injuries to the developing brain are sometimes followed by rebounds of neurogenesis (e.g., Andreoli, J. et al., *Am. J. Anat.* 137, 87 (1973); Bohn, M. C. and Lauder, J. M., *Dev. Neurosci.,* 1, 250 (1978); Bohn, M. C., *Neuroscience,* 5, 2003 (1980)), and it is possible that such rebounds could overshoot the normal cell number. Further, because increased cell density has been observed in the limbic system, the cerebellum is not the only brain region in which some form of overgrowth might account for the neuro-anatomy of autistic cases. It may well be that some autism-inducing injuries occur just prior to a period of rapid growth for the cerebellar lobules in question or the limbic system, leading to excess growth, while other injuries continue to be damaging during the period of rapid growth, leading to hypoplasia. However, the hypothesis that autism occurs with both hypoplastic and hyperplastic cerebella calls into question whether cerebellar anomalies play a major role in autistic symptoms.

A particularly instructive result has appeared in an MRI study on the cerebral cortex (Piven, J. et al., *Am. J. Psychiat.,* 14, 734 (1992)). Of a small sample of autistic cases, the majority showed gyral anomalies (e.g., patches of pachygyria). However, the abnormal areas were not located in the same regions from case to case. That is, while the functional symptoms were similar in all the subjects, the brain damage observed was not. The investigators argue convincingly that the cortical anomalies were not responsible for the functional abnormalities. This is a central problem in all attempts to screen for pathology in living patients or in autopsy cases. While abnormalities may be present, it is not necessarily true that they are related to the symptoms of autism.

To teratologists, the physical anomalies of a neonate, child, or adult can serve as a guide to when the embryo was injured. Years of research have amplified the details of that timetable for the nervous system (Rodier, P. M., *Dev. Med. Child Neurol.,* 22, 525 (1980); Bayer, S. A. et al., *Neurotoxicology,* 14, 83 (1993)). In the case of autism, lack of specific information on the neuroanatomy associated with the disease has made it difficult to estimate the stage of development when the disorder arises. However, in 1993, Miller and Strömland reported a finding that conclusively identified the time of origin for some cases. They observed that the rate of autism was 33% in people exposed to thalidomide between the 20th and 24th days of gestation, and 0% in cases exposed at other times (Strömland, K. et al., *Devel. Med. Child. Neurol.*, 36, 351 (1994)). Their deduction regarding the time of injury was not based on neuroanatomy, which was not known in their living subjects. Instead, it was based on the external stigmata of the cases.

Because thousands of thalidomide-exposed offspring have been evaluated for somatic malformations, the array of injuries associated with the drug is well-known, and the time when each arises has been carefully defined (Miller, M. T., *Trans. Am. Ophthalmol. Soc.*, 89, 623 (1991)). Of five cases of thalidomide-induced autism, four had malformations of the ears, without limb malformation, and the fifth had malformation of the ears, forelimb, and hindlimb. Thalidomide is not teratogenic before the 20th day of gestation. Starting on day 20 exposure causes ear malformation and abnormalities of the thumb. Limb malformations (other than those of the thumb) first appear with exposure on the 25th day, with effects moving from the forelimb to the hindlimb as exposure occurs at later stages. After the 35th day, thalidomide produces no malformations. Thus, the cases with malformations restricted to the ear must have been exposed before day 25, and the one patient with multiple malformations can only be explained as a case of repeated injuries at several stages of development.

In fact, the idea that autism might arise very early in gestation was suggested long ago. Steg and Rapoport (*J. Aut. Child. Schiz.*, 5, 299 (1975)) noted the significant increase in minor physical anomalies among children with autism, and realized that they indicated an injury in the first trimester. Several studies of minor malformations have found ear effects to be the most common anomalies in autism (Walker, H. A., *J. Aut. Child. Schiz.*, 7, 165 (1977); Campbell, M. et al., *Am. J. Psychiat.*, 135, 573 (1978)), and the most recent study shows that they are not only the best discriminator between people with autism and normal controls, but also the only anomaly that discriminates autism from other developmental disabilities (Rodier, P. M. et al., *Teratology* 55, 319 (1997)). Ear anomalies are among the earliest of all minor physical malformations in their time of origin.

External malformations are not the only evidence which puts the time of injury in autism at the time of neural tube closure. The cranial nerve dysfunctions observed in the patients with autism secondary to thalidomide exposure— facial nerve palsy, Duane syndrome (lack of abducens innervation with reinnervation of the lateral rectus by the oculomotor nerve), abnormal lacrimation, gaze paresis, and hearing deficits (Strömland, K. et al., *Devel. Med. Child. Neurol.*, 36, 351 (1994))—suggest that the earliest-forming structures of the brain stem were damaged, and it is now known that these form during neural tube closure (Bayer, S. A. et al., *Neurotoxicology*, 14, 83 (1993)). Subsequent studies have shown that a human brain from a patient with autism has the same pattern of brain stem injury predicted by the thalidomide cases (Rodier, P. M. et al., *J. Comp. Neurol.*, 370, 247 (1996)). Perhaps even more importantly, the autopsied brain has a shortening of the brain stem in the region of the fifth rhombomere, and is missing two of the nuclei known to form from that embryological structure. The rhombomeres exist so briefly (Streeter, G. L., *Contr. Embryol. Carneg. Instn.*, 30,213 (1948)) that the evidence that one failed to form is conclusive in pinpointing the time of injury. Like the thalidomide cases, the autopsy case could have been injured only at the time of neural tube closure.

The effect of injury around neural tube closure has been tested experimentally, to see whether it can produce anatomical results like those suspected in the thalidomide cases and observed in human brain. Animals exposed during the critical period to valproic acid, a teratogen with effects similar to thalidomide, which has also been associated with autism (Christianson, A. L. et al., *Devel. Med. Child. Neurol.*, 36, 357 (1994); Williams, P. G. et al., *Dev. Med. Child. Neurol.*, 39, 632 (1997)) exhibit reductions in the number of cranial nerve motor neurons (Rodier, P. M. et al., *J. Comp. Neurol.*, 370, 247 (1996)). They are distinguished from controls by shortening of the hindbrain in the region which forms from the fifth rhombomere, just as the autopsied brain was (Rodier, P. M., et al., *Teratology* 55, 319 (1997)). Additional data suggests that the animal model has secondary changes in the cerebellum like those reported in some human cases of autism (Ingram, J. L. et al., *Teratology*, 53, 86 (1996)).

It has long been known that heritable factors play an important role in the etiology of autism. This was demonstrated by the original twin studies of Folstein and Rutter (*J. Child Psychol. Psychiat.*, 18, 297 (1977)) and the subsequent addition of more twin pairs to the sample has only increased the estimate of the proportion of cases suspected to have a genetic basis (e.g. Bailey, A. et al., *Psychol. Med.*, 25, 63 (1995); LeCouteur, A. et al., *J. Child Psychol. Psychiat.*, 37, 785 (1996)). Family studies of siblings (Smalley, S. L. et al., *Arch. Gen. Psychiat.*, 45, 953 (1988)) and parents (Landa, R. et al., *J. Speech Hear. Res.*, 34, 1339 (1991); Landa, R. et al., *Psych. Med.*, 22, 245 (1992)) also support the conclusion that an inherited risk is involved in many, perhaps all, cases of autism spectrum disorders. While the rate of autism is elevated in close relatives of cases, the rate of symptoms short of the diagnosis is increased much more. That is, individuals known to share genetic factors seem to vary in the degree to which symptoms are expressed. This non-Mendelian pattern (Jorde, L. B. et al., *Am. J. Hum. Genet.*, 49, 932 (1991)) suggests a complex disorder with major contributions from predisposing genetic factors, which interact with the overall genetic background and/or environmental insults to determine the phenotype.

The ability to identify the genetic factors that increase the risk for autism would be a breakthrough for genetic counseling for prevention of the disorder. In addition, it would allow the creation of genetically-engineered animals in which to study the environmental factors that interact with the inherited predispositions. Tests for genetic factors would also serve as biomarkers, valuable for diagnosis, and useful in research on all aspects of the autism spectrum. Unfortunately, neither linkage nor association studies have revealed any chromosomal regions strongly related to autism (e.g. Spence, M. A. et al., *Behav. Genet.*, 15, 1 (1985); Smalley, S. L. et al., *Arch. Gen. Psychiat.*, 45, 953 (1988); Cook, E. H. et al., *Molec. Psychiat.*, 2, 247 (1997); Klauck, S. M. et al., *Hum. Molec. Genet.*, 6, 2233 (1997); Cook, E. H. et al., *Am. J. Hum. Genet.*, 62, 1077 (1998)).

Furthermore, while there is no known medical treatment for autism, some success has been reported for early intervention with behavioral therapies. A biomarker would allow identification of the disease, now typically diagnosed between ages three and five, in infancy or prenatal life. Thus, there is an urgient need for a method of reliably identifying subjects with autism. In particular there is need for a blood test for polymorphisms causing autism spectrum disorders.

Families with affected members need to know whether they carry a mutation which could affect future pregnancies. Clinicians need a test as an aid in diagnosis, and researchers would use the test to classify subjects according to the etiology of their disease.

SUMMARY OF THE INVENTION

The present invention relates to a method for screening subjects for genetic markers associated with autism. A biological sample is isolated from a mammal and then tested for the presence of a mutated gene or a product thereof which is associated with autism.

Another aspect of the invention is an isolated nucleic acid encoding a HoxA1 allele having a polymorphism which is associated with autism spectrum disorders.

Yet another aspect of the invention is an isolated nucleic acid encoding a HoxB1 allele having a polymorphism which is associated with autism spectrum disorders.

BRIEF DESCRIPTION OF THE DRAWINGS

FIG. 1 shows two different alleles of HoxA1 from a case of autism spectrum disorder.

DETAILED DESCRIPTION OF THE INVENTION

Figure 1A:
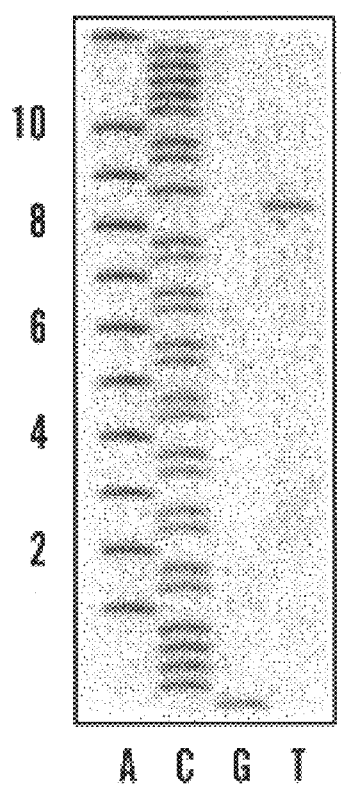
FIG. 1A shows the previously published sequence of wild-type HoxA1.

The present invention provides a method for screening subjects for genetic markers associated with autism. A biological sample is isolated from a mammal and then tested for the presence of a mutated gene or a product thereof which is associated with autism.

Polymorphisms in Hox genes are shown to be associated with autism spectrum disorders. The Hox genes are a family of genes that function in the patterning of body structures that develop along an anteroposterior axis, such as the limbs, skeleton, and nervous system; they are expressed during embryonic development at specific times in limited regions of the embryo. In the mouse, for example, Hox-a1 is expressed in rhombomeres 4 through 8 of the developing hindbrain on days 8 to 8.5 of gestation. The Hox genes control the pattern formation of the hindbrain. Similar abnormalities have been observed in the brains of autistic individuals (Rodier et al., *J. Comp. Neuro.* 370, 247 (1996), which is hereby incorporated by reference).

The DNA and amino acid sequences for HoxA-1 have previously been reported (Acampora, D. et al., *Nucleic Acids Res.*, 17, 10385 (1989); Hong, Y. et al., *Gene,* 159, 209 (1995) which are hereby incorporated by reference). Exon 1 stretches from base 1 to base 357. Exon 2 stretches from base 358 to the end (1008). The wildtype gene sequences for HoxA1 is provided in SEQ. ID. No. 1 as follows:

```
ATGGACAATG CAAGAATGAA CTCCTTCCTG GAATACCCCA TACTTAGCAG TGGCGACTCG        60
GGGACCTGCT CAGCCCGAGC CTACCCCTCG GACCATAGGA TTACAACTTT CCAGTCGTGC       120
GCGGTCAGCG CCAACAGTTG CGGCGGCGAC GACCGCTTCC TAGTGGGCAG GGGGGTGCAG       180
ATCGGTTCGC CCCACCACCA CCACCACCAC CACCATCACC ACCCCCAGCC GGCTACCTAC       240
CAGACTTCCG GGAACCTGGG GGTGTCCTAC TCCCACTCAA GTTGTGGTCC AAGCTATGGC       300
TCACAGAACT TCAGTGCGCC TTACAGCCCC TACGCGTTAA ATCAGGAAGC AGACGTAAGT       360
GGTGGGTACC CCCAGTGCGC TCCCGCTGTT TACTCTGGAA ATCTCTCATC TCCCATGGTC       420
CAGCATCACC ACCACCACCA GGGTTATGCT GGGGGCGCGG TGGGCTCGCC TCAATACATT       480
CACCACTCAT ATGGACAGGA GCACCAGAGC CTGGCCCTGG CTACGTATAA TAACTCCTTG       540
TCCCCTCTCC ACGCCAGCCA CCAAGAAGCC TGTCGCTCCC CCGCATCGGA GACATCTTCT       600
CCAGCGCAGA CTTTTGACTG GATGAAAGTC AAAAGAAACC CTCCCAAAAC AGGGAAAGTT       660
GGAGAGTACG GCTACCTGGG TCAACCCAAC GCGGTGCGCA CCAACTTCAC TACCAAGCAG       720
CTCACGGAAC TGGAGAAGGA GTTCCACTTC AACAAGTACC TGACGCGCGC CCGCAGGGTG       780
GAGATCGCTG CATCCCTGCA GCTCAACGAG ACCCAAGTGA AGATCTGGTT CCAGAACCGC       840
CGAATGAAGC AAAAGAAACG TGAGAAGGAG GGTCTCTTGC CCATCTCTCC GGCCACCCCG       900
CCAGGAAACG ACGAGAAGGC CGAGGAATCC TCAGAGAAGT CCAGCTCTTC GCCCTGCGTT       960
CCTTCCCCGG GGTCTTCTAC CTCAGACACT CTGACTACCT CCCACTGA                  1008
```

The nucleic acid molecule of SEQ. ID. No. 1 encodes a polypeptide having the amino acid sequence of SEQ. ID. No. 2, as follows:

| | | | | | | | | | | | | | | |
|---|---|---|---|---|---|---|---|---|---|---|---|---|---|---|
| M | D | N | A | R | M | N | S | F | L | E | Y | P | I | L | 15 |
| S | S | G | D | S | G | T | C | S | A | R | A | Y | P | S | 30 |
| D | H | R | I | T | T | F | Q | S | C | A | V | S | A | N | 45 |
| S | C | G | G | D | D | R | F | L | V | G | R | G | V | Q | 60 |
| I | G | S | P | H | H | H | H | H | H | H | H | H | H | P | 75 |
| Q | P | A | T | Y | Q | T | S | G | N | L | G | V | S | Y | 90 |
| S | H | S | S | C | G | P | S | Y | G | S | Q | N | F | S | 105 |
| A | P | Y | S | P | Y | A | L | N | Q | E | A | D | V | S | 120 |
| G | G | Y | P | Q | C | A | P | A | V | Y | S | G | N | L | 135 |
| S | S | p | M | V | Q | H | H | H | H | H | Q | G | Y | A | 150 |
| G | G | A | V | G | S | P | Q | Y | I | H | H | S | Y | G | 165 |
| Q | E | H | Q | S | L | A | L | A | T | Y | N | N | S | L | 180 |
| S | P | L | H | A | S | H | Q | E | A | C | R | S | P | A | 195 |
| S | E | T | S | S | P | A | Q | T | F | D | W | M | K | V | 210 |
| K | R | N | P | P | K | T | G | K | V | G | E | Y | G | Y | 225 |
| L | G | Q | P | N | A | V | R | T | N | F | T | T | K | Q | 240 |
| L | T | E | L | E | K | E | F | H | F | N | K | Y | L | T | 255 |
| R | A | R | R | V | E | I | A | A | S | L | Q | L | N | E | 270 |
| T | Q | V | K | I | W | F | Q | N | R | R | M | K | Q | K | 285 |
| K | R | E | K | E | G | L | L | P | I | S | P | A | T | P | 300 |
| P | G | N | D | E | K | A | E | E | S | S | E | K | S | S | 315 |
| S | S | P | C | V | P | S | P | G | S | S | T | S | D | T | 330 |
| L | T | T | S | H | | | | | | | | | | | 335 |

A polymorphism in the HocA1 gene has been isolated and sequenced. This polymorphism is associated with autism spectrum disorders. A single base substitution is located at position 218 (underlined) of SEQ. ID. No. 3, where an A is changed to a G, as follows:

The single base substitution at position 218 results in the replacement of histidine with arginine (underlined). The resulting protein has the amino acid sequence (SEQ. ID. No. 4) as follows:

```
ATGGACAATG CAAGAATGAA CTCCTTCCTG GAATACCCCA TACTTAGCAG TGGCGACTCG      60
GGGACCTGCT CAGCCCGAGC CTACCCCTCG GACCATAGGA TTACAACTTT CCAGTCGTGC     120
GCGGTCAGCG CCAACAGTTG CGGCGGCGAC GACCGCTTCC TAGTGGGCAG GGGGGTGCAG     180
ATCGGTTCGC CCCACCACCA CCACCACCAC CACCATCGCC ACCCCAGCC  GGCTACCTAC     240
CAGACTTCCG GAACCTGGG  GGTGTCCTAC TCCCACTCAA GTTGTGGTCC AAGCTATGGC     300
TCACAGAACT TCAGTGCGCC TTACAGCCCC TACGCGTTAA ATCAGGAAGC AGACGTAAGT     360
GGTGGGTACC CCCAGTGCGC TCCCGCTGTT TACTCTGGAA ATCTCTCATC TCCCATGGTC     420
CAGCATCACC ACCACCACCA GGGTTATGCT GGGGGCGCGG TGGGCTCGCC TCAATACATT     480
CACCACTCAT ATGGACAGGA GCACCAGAGC CTGGCCCTGG CTACGTATAA TAACTCCTTG     540
TCCCCTCTCC ACGCCAGCCA CCAAGAAGCC TGTCGCTCCC CCGCATCGGA GACATCTTCT     600
CCAGCGCAGA CTTTTGACTG GATGAAAGTC AAAAGAAACC CTCCCAAAAC AGGGAAAGTT     660
GGAGAGTACG GCTACCTGGG TCAACCCAAC GCGGTGCGCA CCAACTTCAC TACCAAGCAG     720
CTCACGGAAC TGGAGAAGGA GTTCCACTTC AACAAGTACC TGACGCGCGC CCGCAGGGTG     780
GAGATCGCTG CATCCCTGCA GCTCAACGAG ACCCAAGTGA AGATCTGGTT CCAGAACCGC     840
CGAATGAAGC AAAAGAAACG TGAGAAGGAG GGTCTCTTGC CCATCTCTCC GGCCACCCCG     900
CCAGGAAACG ACGAGAAGGC CGAGGAATCC TCAGAGAAGT CCAGCTCTTC GCCCTGCGTT     960
CCTTCCCCGG GGTCTTCTAC CTCAGACACT CTGACTACCT CCCACTGA               1008
```

| | | | | | | | | | | | | | | |
|---|---|---|---|---|---|---|---|---|---|---|---|---|---|---|
| M | D | N | A | R | M | N | S | F | L | E | Y | P | I | L | 15 |
| S | S | G | D | S | G | T | C | S | A | R | A | Y | P | S | 30 |
| D | H | R | I | T | T | F | Q | S | C | A | V | S | A | N | 45 |
| S | C | G | G | D | D | R | F | L | V | G | R | G | V | Q | 60 |
| I | G | S | P | H | H | H | H | H | H | H | R | H | P | 75 |
| Q | P | A | T | Y | Q | T | S | G | N | L | G | V | S | Y | 90 |
| S | H | S | S | C | G | P | S | Y | G | S | Q | N | F | S | 105 |
| A | P | Y | S | P | Y | A | L | N | Q | E | A | D | V | S | 120 |
| G | G | Y | P | Q | C | A | P | A | V | Y | S | G | N | L | 135 |
| S | S | P | M | V | Q | H | H | H | H | H | Q | G | Y | A | 150 |
| G | G | A | V | G | S | P | Q | Y | I | H | H | S | Y | G | 165 |
| Q | E | H | Q | S | L | A | L | A | T | Y | N | N | S | L | 180 |
| S | P | L | H | A | S | H | Q | E | A | C | R | S | P | A | 195 |
| S | E | T | S | S | P | A | Q | T | F | D | W | M | K | V | 210 |
| K | R | N | P | P | K | T | G | K | V | G | E | Y | G | Y | 225 |
| L | G | Q | P | N | A | V | R | T | N | F | T | T | K | Q | 240 |
| L | T | E | L | E | K | E | F | H | F | N | K | Y | L | T | 255 |
| R | A | R | R | V | E | I | A | A | S | L | Q | L | N | E | 270 |
| T | Q | V | K | I | W | F | Q | N | R | R | M | K | Q | K | 285 |
| K | R | E | K | E | G | L | L | P | I | S | P | A | T | P | 300 |
| P | G | N | D | E | K | A | E | E | S | S | E | K | S | S | 315 |
| S | S | P | C | V | P | S | P | G | S | S | T | S | D | T | 330 |
| L | T | T | S | H | | | | | | | | | | | 335 |

In addition to the polymorphism in HoxA1, a polymorphism associated with autism spectrum disorders has been isolated and sequenced from the HoxB1 gene. The Hoxb1 gene has not been studied as comprehensively as Hoxa1 in transoenic knockouts, but is expressed at the same stage (Murphy, P et al., *Development*, 111, 61 (1991), which is hereby incorporated by reference). Its null mutation produces similar malformations, including severe diminution of the facial nucleus (Goddard, J. M. et al., *Development*, 122, 3217 (1996), which is hereby incorporated by reference).

The similarity of expression and function of these two genes is due to the fact that they were originally a single gene in invertebrates (Ruddle, F. H. et al., *Annu. Rev. Genet.*, 28, 423 (1993), which is hereby incorporated by reference). In mammals, the two appear on separate chromosomes (human 7 and 17), but the sequence of each of the mammalian genes is similar to the others, and similar to the original single gene from which the two mammalian loci arose. The sequence of the wildtype hoxB1 gene (SEQ. ID. No. 5) follows:

```
TGACGCATGG ACTATAATAG GATGAACTCC TTCTTAGAGT ACCCACTCTG TAACCGGGGA      60
CCCAGCGCCT ACAGCGCCCA CAGCGCCCCA ACCTCCTTTC CCCCAAGCTC GGCTCAGGCG     120
GTTGACAGCT ATGCAAGCGA GGGCCGCTAC GGTGGGGGGC TGTCCAGCCC TGCGTTTCAG     180
CAGAACTCCG GCTATCCCGC CCAGCAGCCG CCTTCGACCC TGGGGGTGCC CTTCCCCAGC     240
TCCGCGCCCT CGGGGTATGC TCCTGCCGCC TGCAGCCCCA GCTACGGGCC TTCTCAGTAC     300
TACCCTCTGG GTCAATCAGA AGGAGACGGA GGCTATTTTC ATCCCTCGAG CTACGGGCC      360
CAGCTAGGGG GCTTGTCCGA TGGCTACGGA GCAGGTGGAG CCGGTCCGGG GCCATATCCT     420
CCGCAGCATC CCCCTTATGG GAACGAGCAG ACCGCGAGCT TTGCACCGGC CTATGCTGAT     480
CTCCTCTCCG AGGACAAGGA AACACCCTGC CCTTCAGAAC CTAACACCCC CACGGCCCGG     540
ACCTTCGACT GGATGAAGGT TAAGAGAAAC CCACCCAAGA CAGCGAAGGT GTCAGAGCCA     600
GGCCTGGGCT CGCCCAGTGG CCTCCGCACC AACTTCACCA CAAGGCAGCT GACAGAACTG     660
GAAAAGGAGT TCCATTTCAA CAAGTACCTG AGCCGGGCCC GGAGGGTGGA GATTGCCGCC     720
ACCCTGGAGC TCAATGAAAC ACAGGTCAAG ATTTGGTTCC AGAACCGACG AATGAAGCAG     780
AAGAAGCGCG AGCGAGAGGG AGGTCGGGTC CCCCCAGCCC CACCAGGCTG CCCCAAGGAG     840
GCAGCTGGAG ATGCCTCAGA CCAGTCGACA TGCACCTCCC CGGAAGCCTC ACCCAGCTCT     900
GTCACCTCCT GAACTGAACC TAGCCACCAA TGGGGCTTCC AGGCACTGGA GCGCCCCAGT     960
CCAGCCCTAT CCCAGGCTCT CCCAACCCAG GCCTGGCTTC ACTGCCTGGG ATCTCTAGGC    1020
T                                                                   1021
```

The protein encoded by nucleotides 7 to 909 of the wild-type HoxB1 gene (SEQ. ID. No. 6) is as follows:

| | | | | | | | | | | | | | | |
|---|---|---|---|---|---|---|---|---|---|---|---|---|---|---|
| M | D | Y | N | R | M | N | S | F | L | E | Y | P | L | C | 15 |
| N | R | G | P | S | A | Y | S | A | H | S | A | P | T | S | 30 |
| F | P | P | S | S | A | Q | A | V | D | S | Y | A | S | E | 45 |
| G | R | Y | D | G | G | L | S | S | P | A | F | Q | Q | N | 60 |
| S | G | Y | P | A | Q | Q | P | P | S | T | L | G | V | P | 75 |
| E | P | S | S | A | P | S | G | Y | A | P | A | A | C | S | 90 |
| P | S | Y | G | P | S | Q | Y | Y | P | L | G | Q | S | E | 105 |
| G | D | G | G | Y | F | H | P | S | S | Y | G | A | Q | L | 120 |
| G | G | L | S | D | G | Y | G | A | G | G | A | G | P | G | 135 |
| P | Y | P | P | Q | H | P | P | Y | G | N | E | Q | T | A | 150 |
| S | F | A | P | A | Y | A | D | L | L | S | E | D | K | E | 165 |
| T | P | C | P | S | E | P | N | T | P | T | A | R | T | E | 180 |
| D | W | M | K | V | K | R | N | P | P | K | T | A | K | V | 195 |
| S | E | P | G | L | G | S | P | S | G | L | R | T | N | F | 210 |
| T | T | R | Q | L | T | E | L | E | K | E | F | H | F | N | 225 |
| K | Y | L | S | R | A | R | R | V | E | I | A | A | T | L | 240 |
| E | L | N | E | T | Q | V | K | I | W | F | Q | N | R | R | 255 |
| M | K | Q | K | K | R | E | R | E | G | G | R | V | P | F | 270 |
| A | P | P | G | C | P | K | E | A | A | G | D | A | S | D | 285 |
| Q | S | T | C | T | S | P | E | A | S | P | S | S | V | T | 300 |
| S | | | | | | | | | | | | | | | 301 |

As with the HoxA1 gene, polymorphisms associated with autism spectrum disorders were found with HoxB1. The HoxB1 mutation occurs after base 88 (C) with the insertion of nine nucleotides (ACAGCGCCC). The location of this insertion is such that the amino acid sequence also changes. The normal sequence reads . . . serine-alanine-histidine-serine-alanine-proline. The mutant sequence has an extra serine-alanine-histidine-sequence and then the sequence resumes normally. The insertion and altered amino acid sequence are underlined below. A mutated form of HoxB1 (SEQ. ID. No. 7) is depicted as follows:

```
TGACGCATGG ACTATAATAG GATGAACTCC TTCTTAGAGT ACCCACTCTG TAACCGGGGA    60
CCCAGCGCCT ACAGCGCCCA CAGCGCCCAC AGCGCCCCAA CCTCCTTTCC CCCAAGCTCG   120
GCTCAGGCGG TTGACAGCTA TGCAAGCGAG GGCCGCTACG GTGGGGGCT  GTCCAGCCCT   180
GCGTTTCAGC AGAACTCCGG CTATCCCGCC CAGCAGCCGC CTTCGACCCT GGGGGTGCCC   240
TTCCCCAGCT CCGCGCCCTC GGGGTATGCT CCTGCCGCCT GCAGCCCCAG CTACGGGCCT   300
TCTCAGTACT ACCCTCTGGG TCAATCAGAA GGAGACGGAG GCTATTTTCA TCCCTCGAGC   360
TACGGGGCCC AGCTAGGGGG CTTGTCCGAT GGCTACGGAG CAGGTGGAGC CGGTCCGGGG   420
CCATATCCTC CGCAGCATCC CCCTTATGGG AACGAGCAGA CCGCGAGCTT TGCACCGGCC   480
TATGCTGATC TCCTCTCCGA GGACAAGGAA ACACCCTGCC CTTCAGAACC TAACACCCCC   540
ACGGCCCGGA CCTTCGACTG GATGAAGGTT AAGAGAAACC CACCCAAGAC AGCGAAGGTG   600
TCAGAGCCAG GCCTGGGCTC GCCCAGTGGC CTCCGCACCA ACTTCACCAC AAGGCAGCTG   660
ACAGAACTGG AAAAGGAGTT CCATTTCAAC AAGTACCTGA GCCGGGCCCG GAGGGTGGAG   720
ATTGCCGCCA CCCTGGAGCT CAATGAAACA CAGGTCAAGA TTTGGTTCCA GAACCGACGA   780
ATGAAGCAGA AGAAGCGCGA GCGAGAGGGA GGTCGGGTCC CCCCAGCCCC ACCAGGCTGC   840
CCCAAGGAGG CAGCTGGAGA TGCCTCAGAC CAGTCGACAT GCACCTCCCC GGAAGCCTCA   900
CCCAGCTCTG TCACCTCCTG AACTGAACCT AGCCACCAAT GGGGCTTCCA GGCACTGGAG   960
CGCCCCAGTC CAGCCCTATC CCAGGCTCTC CCAACCCAGG CCTGGCTTCA CTGCCTGGGA  1020
TCTCTAGGCT                                                        1030
```

The protein encoded by SEQ. ID. No. 8 is as follows:

| M | D | Y | N | R | M | N | S | F | L | E | Y | P | L | C | 15 |
|---|---|---|---|---|---|---|---|---|---|---|---|---|---|---|---|
| N | R | G | P | S | A | Y | S | A | H | S | A | H | S | A | 30 |
| P | T | S | F | P | P | S | S | A | Q | A | V | D | S | Y | 45 |
| A | S | E | G | R | Y | G | G | G | L | S | S | P | A | F | 60 |
| Q | Q | N | S | G | Y | P | A | Q | Q | P | P | S | T | L | 75 |
| G | V | P | F | P | S | S | A | P | S | G | Y | A | P | A | 90 |
| A | C | S | P | S | Y | G | P | S | Q | Y | Y | P | L | G | 105 |
| Q | S | E | G | D | G | G | Y | F | H | P | S | S | Y | G | 120 |
| A | Q | L | G | G | L | S | D | G | Y | G | A | G | G | A | 135 |
| G | P | G | P | Y | P | P | Q | H | P | P | Y | G | N | E | 150 |
| Q | T | A | S | F | A | P | A | Y | A | D | L | L | S | E | 165 |
| D | K | E | T | P | C | P | S | E | P | N | T | P | T | A | 180 |
| R | T | F | D | W | M | K | V | K | R | N | P | P | K | T | 195 |
| A | K | V | S | E | P | G | L | G | S | P | S | G | L | R | 210 |
| T | N | F | T | T | R | Q | L | T | E | L | E | K | E | F | 225 |
| H | F | N | K | Y | L | S | R | A | R | R | V | E | I | A | 240 |
| A | T | L | E | L | N | E | T | Q | V | K | I | W | F | Q | 255 |
| N | R | R | M | K | Q | K | K | R | E | R | E | G | G | R | 270 |
| V | P | P | A | P | P | G | C | P | K | E | A | A | G | D | 285 |
| A | S | D | Q | S | T | C | T | S | P | E | A | S | P | S | 300 |
| S | V | T | S | | | | | | | | | | | | 304 |

Genes which have been duplicated and then maintained similar functions over the course of evolution are called "paralogs." A third paralog derived from the same invertebrate gene is known as HoxD1. This gene has not yet been studied in knockouts, but is known to have evolved to be expressed in somewhat different embryonic tissues (mesoderm vs. ectoderm) in the hindbrain region at the same stage of development as Hoxa1 and Hoxb1. Thus preferred hox genes include HoxA1, HoxB1, and HoxD1.

Biological samples suitable for testing include blood, saliva, amniotic fluid, and tissue. The most preferred biological sample is blood. However, any biological sample from which genetic material or the products of the marker genes can be isolated is suitable.

Because the Hox genes are highly conserved among species, the present invention is applicable for screening for autism related polymorphisms in mammals. The screening method can be utilized to identify animals carrying defects in genes like those which give rise to autism in humans in order to study the progression of the disease and test treatments. However, the preferred mammal to be screened is humans. In particular, the biological samples are isolated from developmentally disabled children or adults in order to determine whether they carry the marker associated with autism to assist in diagnosing the disease. Similarly, the parents or relatives of disabled children may be screened to determine whether they are carriers of the mutated gene. Samples may also be tested from children including infants to identify those children who have genetic markers associated with autism in order to provide them with early behavior training.

As discussed more fully in the examples, polymorphisms in the HoxA1 gene are associated with autism spectrum disorders. In addition to HoxA1, the HoxB1 and HoxD1 genes are also involved in the same stages of early brain development. Hoxb1 and Hoxd1 are related developmental genes which are expressed at the same time and in approximately the same region of the embryo as Hoxa1. The Hox genes are closely related and may perform similar functions in development. Evolutionarily the various Hox genes were probably derived from a common ancestral gene. Thus, the preferred genes to be screened include Hoxa1, Hoxb1, and Hoxd1.

The mutation in the mutated gene may be a single base substitution mutation resulting in an amino acid substitution, a single base substitution mutation resulting in a translational stop, an insertion mutation, a deletion mutation, or a gene rearrangement. As demonstrated from the identified polymorphisms in HoxA1 and HoxB1, polymorphisms which disrupt the gene or result in an altered peptide are associated with autism spectrum disorders.

The mutation may be located in an intron, an exon of the gene, or a promotor or other regulatory region which affects the expression of the gene.

Methods for screening for mutated nucleic acids include direct sequencing of nucleic acids, single strand polymorphism assay, ligase chain reaction, enzymatic cleavage, and southern hybridization.

Screening for mutated nucleic acids can be accomplished by direct sequencing of nucleic acids. In fact, putative mutants identified by other methods may be sequenced to determine the exact nature of the mutation. Nucleic acid sequences can be determined through a number of different techniques which are well known to those skilled in the art. In order to sequence the nucleic acid, sufficient copies of the material must first be amplified.

Amplification of a selected, or target, nucleic acid sequence may be carried out by any suitable means. (See generally Kwoh, D. and Kwoh, T., *Am Biotechnol Lab,* 8, 14 (1990), which is hereby incorporated by reference.) Examples of suitable amplification techniques include, but are not limited to, polymerase chain reaction, ligase chain reaction (see Barany, *Proc Natl Acad Sci USA* 88, 189 (1991), which is hereby incorporated by reference), strand displacement amplification (see generally Walker, G. et al., *Nucleic Acids Res.* 20, 1691 (1992); Walker. G. et al., *Proc Natl Acad Sci USA* 89, 392 (1992), which are hereby incorporated by reference), transcription-based amplification (see Kwoh, D. et al., *Proc Natl Acad Sci USA ,* 86, 1173 (1989), which is hereby incorporated by reference), self-sustained sequence replication (or "3SR") (see Guatelli, J. et al., *Proc Natl Acad Sci USA ,* 87, 1874 (1990), which is hereby incorporated by reference), the Qβ replicase system (see Lizardi, P. et al., *Biotechnology,* 6, 1197 (1988), which is hereby incorporated by reference), nucleic acid sequence-based amplification (or "NASBA") (see Lewis, R., *Genetic*

*Engineering News*, 12(9), 1 (1992), which is hereby incorporated by reference), the repair chain reaction (or "RCR") (see Lewis, R., *Genetic Engineering News*, 12(9), 1 (1992), which is hereby incorporated by reference), and boomerang DNA amplification (or "BDA") (see Lewis, R., *Genetic Engineering News*, 12(9), 1 (1992), which is hereby incorporated by reference). Polymerase chain reaction is currently preferred.

In general, DNA amplification techniques such as the foregoing involve the use of a probe, a pair of probes, or two pairs of probes which specifically bind to DNA encoding the gene of interest, but do not bind to DNA which does not encode the gene, under the same hybridization conditions, and which serve as the primer or primers for the amplification of the gene of interest or a portion thereof in the amplification reaction.

Nucleic acid sequencing can be performed by chemical or enzymatic methods. The enzymatic method relies on the ability of DNA polymerase to extend a primer, hybridized to the template to be sequenced, until a chain-terminating nucleotide is incorporated. The most common methods utilize didoexynucleotides. Primers may be labelled with radioactive or fluorescent labels. Various DNA polymerases are available including Klenow fragment, AMV reverse transcriptase, Thermus aquaticus DNA polymerase, and modified T7 polymerase.

Although DNA sequencing is clearly the most sensitive and informative method, it is too cumbersome for routine use in searching for polymorphisms, especially when the DNA segment of interest is large. Several other methods are available for a rapid search for changes in autism associated genes.

Recently, single strand polymorphism assay ("SSPA") analysis and the closely related heteroduplex analysis methods have come into use as effective methods for screening for single-base polymorphisms (Orita, M. et al., *Proc Natl Acad Sci USA*, 86, 2766 (1989), which is hereby incorporated by reference). In these methods, the mobility of PCR-amplified test DNA from clinical specimens is compared with the mobility of DNA amplified from normal sources by direct electrophoresis of samples in adjacent lanes of native polyacrylamide or other types of matrix gels. Single-base changes often alter the secondary structure of the molecule sufficiently to cause slight mobility differences between the normal and mutant PCR products after prolonged electrophoresis.

Ligase chain reaction is yet another recently developed method of screening for mutated nucleic acids. Ligase chain reaction (LCR) is also carried out in accordance with known techniques. LCR is especially useful to amplify, and thereby detect, single nucleotide differences between two DNA samples. In general, the reaction is called out with two pairs of oligonucleotide probes: one pair binds to one strand of the sequence to be detected; the other pair binds to the other strand of the sequence to be detected. The reaction is carried out by, first, denaturing (e.g., separating) the strands of the sequence to be detected, then reacting the strands with the two pairs of oligonucleotide probes in the presence of a heat stable ligase so that each pair of oligonucleotide probes hybridize to target DNA and, if there is perfect complementarity at their junction, adjacent probes are ligated together. The hybridized molecules are then separated under denaturation conditions. The process is cyclically repeated until the sequence has been amplified to the desired degree. Detection may then be carried out in a manner like that described above with respect to PCR.

Southern hybridization is also an effective method of identifying differences in sequences. Hybridization conditions, such as salt concentration and temperature can be adjusted for the sequence to be screened. Southern blotting and hybridizations protocols are described in *Current Protocols in Molecular Biology* (Greene Publishing Associates and Wiley-Interscience), pages 2.9.1–2.9.10. Probes can be labelled for hybridization with random oligomers (primarily 9-mers) and the Klenow fragment of DNA polymerase. Very high specific activity probe can be obtained using commercially available kits such as the Ready-To-Go DNA Labelling Beads (Pharmacia Biotech), following the manufacturer's protocol. Briefly, 25 ng of DNA (probe) is labelled with $^{32}$P-dCTP in a 15 minute incubation at 37° C. Labelled probe is then purified over a ChromaSpin (Clontech) nucleic acid purification column. Possible competition of probes having high repeat sequence content, and stringency of hybridization and washdown will be determined individually for each probe used. Alternatively, fragments of a candidate gene may be generated by PCR, the specificity may be verified using a rodent-human somatic cell hybrid panel, and subcloning the fragment. This allows for a large prep for sequencing and use as a probe. Once a given gene fragment has been characterized, small probe preps can be done by gel- or column-purifying the PCR product.

These mismatch detection protocols use samples generated by PCR and thus require use of very little genomic template. All of these methods can provide very good clues regarding the location of the sequence change which leads to the appearance of anomalous bands, hence facilitating subsequent cloning and sequencing strategies.

Methods of screening for mutated nucleic acids can be carried out using either deoxyribonucleic acids ("DNA") or messenger ribonucleic acids ("mRNA") isolated from the biological sample. During periods when the gene is expressed, mRNA may be abundant and more readily detected. However, these genes are temporally controlled and, at most stages of development, the preferred material for screening is DNA.

Alternatively, the detection of a mutated gene associated with autism can be carried out by collecting a biological sample and testing for the presence or form of the protein produced by the gene. The mutation in the gene may result in the production of a mutated form of the peptide or the lack of production of the gene product. In this embodiment, the determination of the presence of the polymorphic form of the protein can be carried out, for example, by isoelectric focusing, protein sizing, or immunoassay. In an immunoassay, an antibody that selectively binds to the mutated protein can be utilized (for example, an antibody that selectively binds to the mutated form of HoxA1 encoded protein). Such methods for isoelectric focusing and immunoassay are well known in the art, and are discussed in further detail below.

Changes in the size or charge of the polypeptide can be identified by isoelectric focusing or protein sizing techniques. Changes resulting in amino acid substitutions, where the substituted amino acid has a different charge than the original amino acid, can be detected by isoelectric focusing. Isoelectric focusing of the polypeptide through a gel having an ampholine gradient at high voltages separates proteins by their pI. The pH gradient gel can be compared to a simultaneously run gel containing the wild-type protein. Protein sizing techniques such as protein electrophoresis and sizing chromatography can also be used to detect changes in the size of the product.

As an alternative to isoelectric focusing or protein sizing, the step of determining the presence of the mutated polypeptides in a sample may be carried out by an antibody assay with an antibody which selectively binds to the mutated polypeptides (i.e., an antibody which binds to the mutated polypeptides but exhibits essentially no binding to the wild-type polypeptide without the polymorphism in the same binding conditions).

Antibodies used to bind selectively the products of the mutated genes can be produced by any suitable technique. For example, monoclonal antibodies may be produced in a hybridoma cell line according to the techniques of Kohler and Milstein, Nature, 265, 495 (1975), which is hereby incorporated by reference. A hybridoma is an immortalized cell line which is capable of secreting a specific monoclonal antibody. The mutated products of genes which are associated with autism may be obtained from a human patient, purified, and used as the immunogen for the production of monoclonal or polyclonal antibodies. Purified polypeptides may be produced by recombinant means to express a biologically active isoform, or even an immunogenic fragment thereof may be used as an immunogen. Monoclonal Fab fragments may be produced in Escherichia coli from the known sequences by recombinant techniques known to those skilled in the art. (See, e.g., Huse, W., Science 246, 1275 (1989), which is hereby incorporated by reference) (recombinant Fab techniques).

The term "antibodies" as used herein refers to all types of immunoglobulin, including IgG, IgM, IgA, IgD, and IgE. The antibodies may be monoclonal or polyclonal and may be of any species of origin, including (for example) mouse, rat, rabbit, horse, or human, or may be chimeric antibodies, and include antibody fragments such as, for example, Fab, F(ab')$_2$, and Fv fragments, and the corresponding fragments obtained from antibodies other than IgG.

Antibody assays may, in general, be homogeneous assays or heterogeneous. In a homogeneous assay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, radioisotopes, fluorescent dyes, enzymes, bacteriophages, coenzymes, and so forth.

In a heterogeneous assay approach, the reagents are usually the specimen, the antibody of the invention and means for producing a detectable signal. Similar specimens as described above may be used. The antibody is generally immobilized on a support, such as a bead, plate, or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Those skilled in the art will be familiar with numerous specific immunoassay formats and variations thereof which may be useful for carrying out the method disclosed herein. See U.S. Pat. Nos. 4,727,022, 4,659,678, 4,376,110, 4,275,149, 4,233,402, and 4,230,767.

Antibodies which selectively bind a polymorphic DLST isoform may be conjugated to a solid support suitable for a diagnostic assay (e.g., beads, plates, slides or wells formed from materials such as latex or polystyrene) in accordance with known techniques, such as precipitation. Antibodies which bind a polymorphic DLST isoform may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

The invention further provides an isolated nucleic acid molecule which encodes a HoxA1 gene having a single base substitution at nucleotide 218 in SEQ. ID. No. 1. In another embodiment, the invention provides an isolated nucleic acid molecule which encodes a HoxB1 gene having an insertion between positions nucleotides 88 and 89 in SEQ. ID. No. 5. In addition, the invention provides fragments of the HoxA1 and HoxB1 genes having the polymorphism, where the fragment has at least 15 nucleotides and encompasses the polymorphism, i.e., the single base substitution. Fragments longer than 15 nucleotides can be used to probe for nucleic acid molecules containing the polymorphism. Longer fragments may be used at higher stringency conditions.

The invention also provides isolated polypeptides that are encoded by the genes having the polymorphisms. Either the whole protein or fragments thereof may be used to induce the production of antibodies specific to the portion of the protein which is effected by the polymorphism. Such antibodies may then be used to detect the presence of a polymorphism. Preferred antibodies bind specifically to the protein or polypeptide effected by the polymorphism but with less affinity to the wild-type Hox protein.

In one embodiment, the antibody is a monoclonal antibody. For use in an immunoassay, the antibody can be bound to a solid support or bound to a detectable label.

EXAMPLES

Example 1

Collection of Blood Samples from Autistic Individuals

Blood was collected from patients with autism and their immediate family members in order to determine whether any polymorphisms in HoxA1 are present among this population. All blood samples were procured following written consent by the patients or their guardians. Among the samples collected were those of the members of a family of four in which one child has autism and the other has Asperger's syndrome; both children have malformed ears. The first son is retarded and the second has normal intelligence. The parents have no obvious symptoms. DNA was extracted from the blood by phenolchloroform extraction following isolation and lysis of the white blood cells. Control DNA was also used for these excrements; this DNA was obtained from neurologically normal donors.

The 20 cc blood samples were left for three–four days at room temperature to allow continued proliferation of white blood cells. White cells were pelleted, followed by isolation of the nuclei. The nuclei were then incubated overnight at 37° C. in a lysis buffer consisting of EDTA, TNE-SDS, and proteinase K. Protein contaminants were extracted by additions of buffered phenol followed by chloroform, then DNA was precipitated by the addition of ice-cold ethanol. The DNA was resuspended in TE buffer for storage at 4° C. Extraction of genomic DNA from fixed tissue was carried out using the protocol of Volkenandt et al., *Methods in Molecular Biology*, 15, 81, Humana Press, (1993), which is hereby incorporated by reference).

Example 2
Sequencing the Hoxa1 Gene

The HoxA1 gene was amplified by PCR from DNA samples to provide sufficient material for sequencing. Two sets of oligonucleotide primers were selected after examination of the human HoxA1 nucleic acid sequence and comparison of the sequence to those of human and mouse Hox genes. The first set was designed to amplify residues 10–647, the second to amplify from residue 656 to the stop codon at residue 1008, exons 1 and 2 of HoxA1, respectively. The primers were used in polymerase chain reaction to amplify the target gene in several control blood samples, in order to determine the appropriate PCR conditions. Both exons were amplified by 94° C. denaturation for 1 min, 62° C., annealing for 30 sec, and 72° C. extension for 2 min, for 35 cycles. The products were visualized with ethidium bromide staining on a 1–2% agarose gel. PhiX174 RF DNA/Hae III fragments (Gibco) were used as a molecular weight marker. The products were tested for chromosome origin by using human-rodent monochromosomal somatic cell hybrids. Both exons amplified by the HoxA1 primers amplified the hybrid containing human chromosome 7 and do not amplify from any other hybrids. Establishing that the product amplified by the primers is from the correct chromosome rules out the possibility that pseudogenes with the same sequence occur at other sites or that the amplified product is another homologous homeobox gene. It verifies that the PCR product represents only the targeted gene.

The polymerase chain reaction (PCR) was performed with various samples of control DNA in order to determine the appropriate conditions. Once the optimal conditions were ascertained, the gene was amplified from the patient samples.

Following PCR, an aliquot of the product was used for DNA sequencing using the Sequenase system version 2.0 (United States Biochemical), which is a chain-termination method of DNA sequencing. The following procedure was used to read the nucleic acid sequence of the amplified products. 7 $\mu$l of PCR product was mixed with 2 $\mu$l shrimp alkaline phosphatase and 0.5 $\mu$l exonuclease I. The mixture was incubated at 37° C. for 15 min and then at 80° C. for 15 min. After addition of 1 $\mu$l of primer, the mixture was incubated at 100° C. for 3 min and then chilled on ice for 5 min. Next, the sample was incubated for 5 min at room temperature with the following additions: 2 $\mu$l 5× buffer, 1 $\mu$l DTT, 2 $\mu$l diluted dGTP, 0.5 $\mu l^{35}$S-dATP, and 2 $\mu$l diluted Sequenase buffer. A 3.5 $\mu$l aliquot of the mixture was then added to 1 $\mu$l of one dideoxyNTP. After 5 min at 37° C., 4 $\mu$l of stop solution was added to the tube. The products were run on a 6% polyacrylamide sequencing gel for 2–4 hr. Following this, the gel was dried on a BioRad gel dryer and exposed to film overnight. Film was developed on a Kodak M35A X-OMAT Processor. The method has been used successfully to duplicate the published sequence of the Hoxa1 exons in samples from a number of controls. The film was developed the next afternoon, and the DNA sequence was read manually for comparison to the published Hox A1 sequence.

The nucleotide sequence from some patients, including the members of the family mentioned previously, showed the presence of two discrete bands at the same levels on the gel.

Example 3
Sequencing the PCR Products

Since sequencing PCR products allows the DNA sequence to be read from both alleles, a sequence with double bands suggests heterozygosity—that the two alleles are not the same and that two different sequences superimposed on one another are being read. Based on these results, the PCR products were cloned in order to get a cleaner sequence. Cloning separates the two alleles and allowed each to be individually sequenced to determine whether one or both alleles are abnormal.

The PCR products were cloned using Invitrogen's Zero Blunt PCR Cloning Kit. This kit is designed to clone blunt-ended PCR fragments, which can be generated by using a thermostable DNA polymerase with proofreading activity. Once the products were cloned, the clonal DNA was sequenced using the Sequenase version 2.0 chain-termination sequencing system. Each clone was sequenced in both 5' and 3' directions, and the reactions were run out for 6 hours on a 6% polyacrylamide sequencing gel.

Figure 1B:
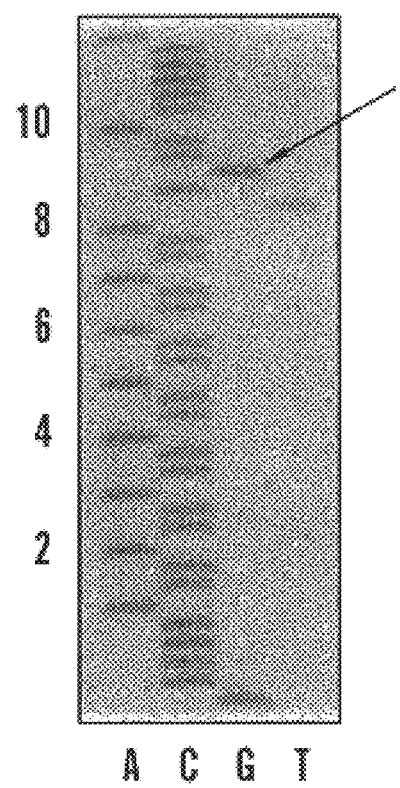
FIG. 1B shows a previously unknown polymorphism having a single base substitution at position 218, where an A is changed to a G.
Figure 2A:
FIG. 2 shows a second polymorphism was identified in the first exon of HoxB1. The published sequence of wild-type HoxB1 (FIG. 2A) is compared to the previously unknown polymorphism in this paralog of HoxA1 (FIG. 2B). In this case, the anomaly is a nine-base insertion that adds a third repeat where two are normally present. The result is three extra amino acids, (serine-alanine-histidine). For each of the polymorphisms, it was possible to test for the presence of the allele different from the known sequence by digesting PCR product with a restriction enzyme (Hph-I for HoxA1 and Msp-I for HoxB1). Sequencing reactions were carried out on 30–40 subjects to be certain that the digestion results match the sequencing results, demonstrating that the digestion procedure detects the deviant sequence described and no other.
Figure 2B:
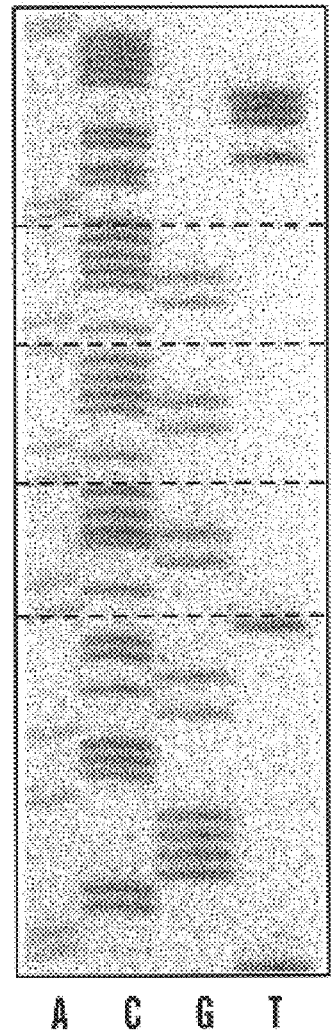

Cloning allowed the determination that three out of four members of this family are indeed heterozygous for Hox A 1. The father and both children contain an identical mutation in the gene: a single base-pair change of A to G in the first exon of the gene; the mother's gene is normal. This mutation is dominant with variable penetrance. Sequences showing the mutation can be seen in FIG. 1. FIG. 1A shows the wild-type sequence. Substitution of guanine for adenine at this single location as shown in FIG. 1B causes an alteration in the resulting amino acid sequence, changing a histidine to an arginine.

Example 4
Restriction Analysis of PCR Products

The PCR products from this family were also subjected to restriction enzyme digestion to confirm the mutation. The enzyme Hph I recognizes the specific sequence 3' . . . CCACT($N_7$) . . . 5'. When normal HoxA1 is digested with this enzyme, it will be cut; however, when mutated HoxA1 is digested, it will not be cut, because the recognition site has been changed by the mutation. This enzyme has been used to digest PCR products from this family and confirm that the mutation does indeed exist in the father and the children but not in the mother. This enzyme has been used to digest PCR products from approximately 100 controls, 36 parent pairs, 26 affected relatives, and 46 probands. In forty cases, the results of the restriction analysis has been compared to that from the sequencing reactions. The two methods gave identical results in every case.

Example 5
Sequencing of a Polymorphism in HoxB1

The sequence for the HoxB1 gene (accession number X16666) was obtained from the Entrez data base. From this sequence primers for the amplification of a 575 bp product of exon 1 by PCR were designed (Sense: 5'-GCATGGACTATAATAGGATG-3' (SEQ. ID. No. 9); Antisense: 5'-TCTTGGGTGGGTTTCTCTTA-3' (SEQ. ID. No. 10)). The final concentration of the following components were used in the amplification reaction: 1.5 U Taq polymerase; 200 $\mu$M each of dATP, dCTP, dGTP, dTTP; 1.5 mM MgCl; 0.4 mM of each sense and antisense primer; 50–100 ng DNA template; and distilled $H_2O$ to a final volume of 25 $\mu$l. The Taq, dNTPs and MgCl are supplied in a Ready-To-Go PCR Bead (Pharmacia 27-9555-01) and were used according to manufacturer's directions. The PCR reaction was carried out in a Perkin-Elmer 480 GeneAmp or a Perkin-Elmer 2400 thermocycler. Reaction conditions were: denaturing for 1 minute at 94° C., and then 35 cycles of denaturing at 94° C. for 45 sec, annealing at 57°C. for 45 sec, and elongation at 72° C. for 45 sec. Resulting PCR product was analyzed on a 1% agarose gel and compare to a 100 bp ladder to determine the size of the product. Since the size of the product was as expected (575 bp) and somatic cell hybrid results indicated that the product is specific for chromosome 17 DNA samples from probands, family members and controls were amplified and sequenced using a radiolabeled terminator cycle sequencing kit (Amersham Life Science US79750). The sequencing reaction was ran on a 6% acrylamide sequencing gel (National Diagnostics) and exposed to Kodak Biomax MS X ray film for 24–48 hours. After developing the film, the resulting sequence was compared to the published sequence found in the Entrez data base.

Example 6

Association of the Newly-discovered Alleles with Autism Spectrum Disorders

Forty-six probands with autistic spectrum disorders and evidence of genetic causation were selected for analysis. Forty-three had one or more other affected family members and thirty-five had ear anomalies or neurological deficits consistent with malfunction of HoxA1 or its paralogs. For comparison, three other groups were tested:

1) An unstructured control group consisting of adults with no evidence of neurological abnormality collected from many different medical centers. These were mostly spouses of patients with late onset degenerative diseases of the nervous system. The purpose of this group was to determine the frequency of the alleles in the general population.

2) Parent controls—While each of the parents of a proband obviously transmits half of his or her genetic material to the proband, imaginary individuals with two alleles constructed from the <u>untransmitted</u> allele of each parent pair should give an accurate estimate of the frequency of the alleles in the study population, aside from those transmitted to the probands. Thus, the untransmitted alleles of the parent pair make a more stringent control, taking into account known and unknown structure in the local population.

3) Affected family members of probands—When they were available, the siblings, cousins, parents, or aunts and uncles of probands diagnosed with autism spectrum disorders or related symptoms (e.g. learning disabilities, language delays, neurological anomalies of the cranial nerves) were tested. If an allele is associated with autism, it should be more frequent in probands and affected family members than in historic or parent controls.

TABLE 1

Percent of individuals with polymorphic forms of HoxA1 and/or B1

|  | HOXA1 | HOXB1 | HOXA1 or HOXB1 |
| --- | --- | --- | --- |
| Historic controls (N = 101) | 16 | 34 | 47 |
| Parent controls (N = 36) | 22 | 39 | 55† |
| Probands with ASD (N = 46) | 35** | 52* | 80*** |
| Other affected relatives (N = 24) | 38* | 42 | 75* | different from historical controls: * = p < .05,  = p < .01, * = p < .001
different from probands: † = <.05

Table 1 demonstrates that parent controls are, indeed, similar to historic controls in their rates of the polymorphisms under study, while affected family members are similar to probands. This is especially true when the two functionally-related genes are combined. Eighty percent of probands have one deviation from the normal sequence or the other, while only 47% of historical controls have an anomaly. Parent controls (untranslated alleles) match the historical controls in their rate of abnormal alleles, indicating that the local population is not structured differently from the general population in its rate of these alleles. In contrast, both probands ($\chi^2$=14.83, p<0.001) and other affected family members ($\chi^2$=6.30, p<0.02) differ significantly from historical controls. The probands differ significantly from the parent controls, as well $\chi^2$=4.08, p<0.05). The probands with genetic anomalies of HoxA1 or HoxB1 are concordant with the other affected members of the family in 18/22 cases ($\chi^2$=17.82, p<0.001). Finally, both the HoxA1 and HoxB1 polymorphisms are significantly associated with autism as judged by the Transmission Disequilibrium Test for Association (Spielman and Ewens, 1996), which compares the rate of transmission "into the disease" to the 50% rate one would expect in offspring of parents with the allele of interest. The $\chi^2$s for this test are: HoxA1=5.16, p<0.05; HoxB1=4.67, p<0.05.

In addition to the living probands, it was of interest to determine the genotype of the patient whose brain anatomy first suggested the involvement of the Hox genes in autism (Rodier et al., 1996). Genomic DNA was extracted from the autopsy tissue, and the patient was determined to have the B1 polymorphism (Stodgell et al., 1998).

One proband is homozygous for the less common allele of HoxA1, and he is severely affected. He was diagnosed early, at 21 months. None of the historic controls, and no parents, were homozygous for the polymorphism. Homozygosity of the HoxB1 polymorphism occurred in two historic controls, one affected parent, and in two severely-affected probands. Larger samples are needed to determine whether either polymorphism reduces viability. Three probands have both polymorphisms, and are severely disabled. The detection and description of the polymorphisms in the first exons of HoxA1 and HoxB1 and the progress of the association studies have been described in a book chapter and two abstracts (Rodier, 1998; Ingram et al., 1997; Stodgell et al., 1998).

Example 7

Identification of a Second Polymorphism in HoxA1

A third polymophism has been detected in the homeobox region of HoxA1 in the second exon. The second exon cannot be amplified by PCR from the DNA of four probands indicating that an anomaly exists. This indicates that they are homozygous for a deviation from the published sequence on which the primers for the exon were based. PCR amplification yields suggest that about ten other probands are heterozygotes for this polymorphism of the second exon of HoxA1.

Additional primers have been developed that will allow complete sequencing of the altered region, which appears to be at the 3' end of the homeobox. Once the sequence is established, a test (such as the use of restriction length polymorphisms) can be developed to allow rapid evaluation of DNA samples. The degree of association of this polymorphism with autism spectrum disorders will then be studied in the same groups already evaluated for the others. Other studies in progress are designed to examine the second exon of HoxB1 and the non-coding regions of both genes.

Example 8

Identification of Additional Polymorphisms in HoxB1 and HoxD1 Associated with Autism The procedures for evaluating the candidate gene HoxD1, as well as for finding additional polymorphisms in HoxA1 and HoxB1, will be the same as for those already identified in HoxA1 and HoxB1. Mutation detection in the coding sequence of these genes will consist of PCR amplification, cloning and sequencing. Mutation detection for the entire genes will include large deletion/insertion analysis by Southern blotting, analysis of 200–400 bp fragments by SSCP or heteroduplex analysis, and of course cloning and sequencing when heterozygosity becomes apparent for any region of the genes. *Current Protocols in Human Genetics* (John Wiley & Sons, Inc.), Chapter 7, "Searching Candidate Genes for Mutations."

Biological samples already isolated from patients with autism which did not show any abnormalities in HoxA1 or HoxB1 will be screened for polymorphisms in HoxD1.

Although preferred embodiments have been depicted and described in detail herein, it will be apparent to those skilled in the relevant art that various modifications, additions, substitutions, and the like can be made without departing from the spirit of the invention and these therefore are considered within the scope of the invention as defined in the claims which follow.

What is claimed:

1. A method for screening subjects for genetic markers associated with autism, comprising:
    isolating a biological sample from a mammal; and
    testing the sample or genetic material isolated from the sample for a polymorphism in a Hox A1 or B1 coding sequence which is a genetic marker for autism.

2. The method according to claim 1, wherein the biological sample is selected from the group consisting of blood, saliva, amniotic fluid, and tissue.

3. The method according to claim 2, wherein the biological sample is blood.

4. The method according to claim 1, wherein the mammal is a human.

5. The method according to claim 4, wherein the biological sample is isolated from developmentally disabled children.

6. The method according to claim 4, wherein the biological sample is isolated from parents or relatives of developmentally disabled children.

7. The method according to claim 4, wherein the biological sample is isolated from children and said method further comprises:

early behavior training for children having genetic markers associated with autism.

8. The method according to claim 1, wherein the polymorphism is located in the homeobox.

9. The method according to claim 1, wherein the coding sequence has a single base substitution resulting in an amino acid substitution.

10. The method according to claim 9, wherein the amino acid substitution is an arginine for a histidine.

11. The method according to claim 10, wherein the coding sequence has an insertion.

12. The method according to claim 11, wherein the insertion is 5' ACAGCGCCC-3'.

13. The method according to claim 1, wherein the coding sequence has a polymorphism selected from the group consisting of a single base substitution resulting in an amino acid substitution, a single base substitution resulting in a translational stop, an insertion, a deletion, and a rearrangement.

14. The method according to claim 1, wherein the polymorphism alters the sequence of the polypeptide encoded by the coding sequence.

15. The method according to claim 1, wherein said screening for mutated nucleic acids is carried out by a method selected from the group consisting of direct sequencing of nucleic acids, single strand polymorphism assay, restriction fragment length polymorphism assay, ligase chain reaction, enzymatic cleavage and southern hybridization.

16. The method according to claim 15, wherein said screening is carried out by direct sequencing of nucleic acids.

17. The method according to claim 15, wherein said screening is carried out by single strand polymorphism assay.

18. The method according to claim 15, wherein said screening is carried out by restriction fragment length polymorphism assay.

19. The method according to claim 15, wherein said screening is carried out by ligase chain reaction.

20. The method according to claim 15, wherein said screening is carried out by enzymatic cleavage.

21. The method according to claim 15, wherein said screening is carried out by southern hybridization.

22. The method according to claim 15, wherein the nucleic acid is a deoxyribonucleic acid.

23. The method according to claim 15, wherein the nucleic acid is a messenger ribonucleic acid.

24. An isolated nucleic acid molecule comprising the nucleotide sequence set forth in SEQ ID NO: 1, wherein the nucleic acid molecule comprises a single base substitution at nucleotide 218.

25. The isolated nucleic acid molecule comprising the nucleotide sequence set forth in SEQ ID NO:5, wherein the nucleic acid molecule comprises an insertion between nucleotides 88 and 89.

26. The isolated nucleic acid molecule according to claim 25, wherein the insertion is 5'-ACAGCGCCC-3'.

27. An isolated nucleic acid molecule consisting of at least 15 contiguous nucleotides of the coding sequence set forth in SEQ ID NO:5 wherein the molecule comprises an insertion between nucleotides 88 and 89 in SEQ ID NO:5 and wherein the molecule specifically binds to a HoxA1 or HoxB1 coding sequence but does not bind to other coding sequences.

28. An isolated nucleic acid molecule consisting of at least 15 contiguous nucleotides of the coding sequence set forth in SEQ ID NO: 1 wherein the molecule comprises a single base substitution at nucleotide 218 and wherein the molecule specifically binds to a HoxA1 or HoxB1 coding sequence but does not bind to other coding sequences.

29. The method according to claim 1 wherein the coding sequence has a mutation in an exon.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1008 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATGGACAATG CAAGAATGAA CTCCTTCCTG GAATACCCCA TACTTAGCAG TGGCGACTCG      60

GGGACCTGCT CAGCCCGAGC CTACCCCTCG GACCATAGGA TTACAACTTT CCAGTCGTGC     120

GCGGTCAGCG CCAACAGTTG CGGCGGCGAC GACCGCTTCC TAGTGGGCAG GGGGGTGCAG     180

ATCGGTTCGC CCCACCACCA CCACCACCAC CACCATCACC ACCCCCAGCC GGCTACCTAC     240

CAGACTTCCG GGAACCTGGG GGTGTCCTAC TCCCACTCAA GTTGTGGTCC AAGCTATGGC     300

TCACAGAACT TCAGTGCGCC TTACAGCCCC TACGCGTTAA ATCAGGAAGC AGACGTAAGT     360

GGTGGGTACC CCCAGTGCGC TCCCGCTGTT TACTCTGGAA ATCTCTCATC TCCCATGGTC     420

CAGCATCACC ACCACCACCA GGGTTATGCT GGGGGCGCGG TGGGCTCGCC TCAATACATT     480

CACCACTCAT ATGGACAGGA GCACCAGAGC CTGGCCCTGG CTACGTATAA TAACTCCTTG     540

TCCCCTCTCC ACGCCAGCCA CCAAGAAGCC TGTCGCTCCC CCGCATCGGA GACATCTTCT     600

CCAGCGCAGA CTTTTGACTG GATGAAAGTC AAAAGAAACC CTCCCAAAAC AGGGAAAGTT     660

GGAGAGTACG GCTACCTGGG TCAACCCAAC GCGGTGCGCA CCAACTTCAC TACCAAGCAG     720

CTCACGGAAC TGGAGAAGGA GTTCCACTTC AACAAGTACC TGACGCGCGC CCGCAGGGTG     780

GAGATCGCTG CATCCCTGCA GCTCAACGAG ACCCAAGTGA AGATCTGGTT CCAGAACCGC     840

CGAATGAAGC AAAAGAAACG TGAGAAGGAG GGTCTCTTGC CCATCTCTCC GGCCACCCCG     900

CCAGGAAACG ACGAGAAGGC CGAGGAATCC TCAGAGAAGT CCAGCTCTTC GCCCTGCGTT     960

CCTTCCCCGG GGTCTTCTAC CTCAGACACT CTGACTACCT CCCACTGA               1008
```

(2) INFORMATION FOR SEQ ID NO:2:

(i) SEQUENCE CHARACTERISTICS:
      (A) LENGTH: 335 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:2:

```
Met Asp Asn Ala Arg Met Asn Ser Phe Leu Glu Tyr Pro Ile Leu Ser
1               5                   10                  15

Ser Gly Asp Ser Gly Thr Cys Ser Ala Arg Ala Tyr Pro Ser Asp His
            20                  25                  30

Arg Ile Thr Thr Phe Gln Ser Cys Ala Val Ser Ala Asn Ser Cys Gly
            35                  40                  45

Gly Asp Asp Arg Phe Leu Val Gly Arg Gly Val Gln Ile Gly Ser Pro
        50                  55                  60

His His His His His His His His Pro Gln Pro Ala Thr Tyr
65                  70                  75                  80

Gln Thr Ser Gly Asn Leu Gly Val Ser Tyr Ser His Ser Ser Cys Gly
                85                  90                  95

Pro Ser Tyr Gly Ser Gln Asn Phe Ser Ala Pro Tyr Ser Pro Tyr Ala
                100                 105                 110

Leu Asn Gln Glu Ala Asp Val Ser Gly Gly Tyr Pro Gln Cys Ala Pro
            115                 120                 125

Ala Val Tyr Ser Gly Asn Leu Ser Ser Pro Met Val Gln His His His
        130                 135                 140

His His Gln Gly Tyr Ala Gly Gly Ala Val Gly Ser Pro Gln Tyr Ile
145                 150                 155                 160

His His Ser Tyr Gly Gln Glu His Gln Ser Leu Ala Leu Ala Thr Tyr
                165                 170                 175

Asn Asn Ser Leu Ser Pro Leu His Ala Ser His Gln Glu Ala Cys Arg
                180                 185                 190

Ser Pro Ala Ser Glu Thr Ser Ser Pro Ala Gln Thr Phe Asp Trp Met
            195                 200                 205

Lys Val Lys Arg Asn Pro Pro Lys Thr Gly Lys Val Gly Glu Tyr Gly
210                 215                 220

Tyr Leu Gly Gln Pro Asn Ala Val Arg Thr Asn Phe Thr Thr Lys Gln
225                 230                 235                 240

Leu Thr Glu Leu Glu Lys Glu Phe His Phe Asn Lys Tyr Leu Thr Arg
                245                 250                 255

Ala Arg Arg Val Glu Ile Ala Ala Ser Leu Gln Leu Asn Glu Thr Gln
            260                 265                 270

Val Lys Ile Trp Phe Gln Asn Arg Arg Met Lys Gln Lys Lys Arg Glu
        275                 280                 285

Lys Glu Gly Leu Leu Pro Ile Ser Pro Ala Thr Pro Pro Gly Asn Asp
290                 295                 300

Glu Lys Ala Glu Glu Ser Ser Glu Lys Ser Ser Ser Ser Pro Cys Val
305                 310                 315                 320

Pro Ser Pro Gly Ser Ser Thr Ser Asp Thr Leu Thr Thr Ser His
            325                 330                 335
```

(2) INFORMATION FOR SEQ ID NO:3:

(i) SEQUENCE CHARACTERISTICS:
        (A) LENGTH: 1008 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

-continued

```
ATGGACAATG CAAGAATGAA CTCCTTCCTG GAATACCCCA TACTTAGCAG TGGCGACTCG      60

GGGACCTGCT CAGCCCGAGC CTACCCCTCG GACCATAGGA TTACAACTTT CCAGTCGTGC     120

GCGGTCAGCG CCAACAGTTG CGGCGGCGAC GACCGCTTCC TAGTGGGCAG GGGGGTGCAG     180

ATCGGTTCGC CCCACCACCA CCACCACCAC CACCATCGCC ACCCCCAGCC GGCTACCTAC     240

CAGACTTCCG GAACCTGGG GGTGTCCTAC TCCCACTCAA GTTGTGGTCC AAGCTATGGC      300

TCACAGAACT TCAGTGCGCC TTACAGCCCC TACGCGTTAA ATCAGGAAGC AGACGTAAGT     360

GGTGGGTACC CCCAGTGCGC TCCCGCTGTT TACTCTGGAA ATCTCTCATC TCCCATGGTC     420

CAGCATCACC ACCACCACCA GGGTTATGCT GGGGGCGCGG TGGGCTCGCC TCAATACATT     480

CACCACTCAT ATGGACAGGA GCACCAGAGC CTGGCCCTGG CTACGTATAA TAACTCCTTG     540

TCCCCTCTCC ACGCCAGCCA CCAAGAAGCC TGTCGCTCCC CCGCATCGGA GACATCTTCT     600

CCAGCGCAGA CTTTTGACTG GATGAAAGTC AAAAGAAACC CTCCCAAAAC AGGGAAAGTT     660

GGAGAGTACG GCTACCTGGG TCAACCCAAC GCGGTGCGCA CCAACTTCAC TACCAAGCAG     720

CTCACGGAAC TGGAGAAGGA GTTCCACTTC AACAAGTACC TGACGCGCGC CCGCAGGGTG     780

GAGATCGCTG CATCCCTGCA GCTCAACGAG ACCCAAGTGA AGATCTGGTT CCAGAACCGC     840

CGAATGAAGC AAAAGAAACG TGAGAAGGAG GGTCTCTTGC CCATCTCTCC GGCCACCCCG     900

CCAGGAAACG ACGAGAAGGC CGAGGAATCC TCAGAGAAGT CCAGCTCTTC GCCCTGCGTT     960

CCTTCCCCGG GGTCTTCTAC CTCAGACACT CTGACTACCT CCCACTGA               1008
```

(2) INFORMATION FOR SEQ ID NO:4:

(i) SEQUENCE CHARACTERISTICS:
        (A) LENGTH: 335 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

```
Met Asp Asn Ala Arg Met Asn Ser Phe Leu Glu Tyr Pro Ile Leu Ser
1               5                  10                  15

Ser Gly Asp Ser Gly Thr Cys Ser Ala Arg Ala Tyr Pro Ser Asp His
            20                  25                  30

Arg Ile Thr Thr Phe Gln Ser Cys Ala Val Ser Ala Asn Ser Cys Gly
        35                  40                  45

Gly Asp Asp Arg Phe Leu Val Gly Arg Gly Val Gln Ile Gly Ser Pro
    50                  55                  60

His His His His His His His Arg His Pro Gln Pro Ala Thr Tyr
65                  70                  75                  80

Gln Thr Ser Gly Asn Leu Gly Val Ser Tyr Ser His Ser Ser Cys Gly
            85                  90                  95

Pro Ser Tyr Gly Ser Gln Asn Phe Ser Ala Pro Tyr Ser Pro Tyr Ala
            100                 105                 110

Leu Asn Gln Glu Ala Asp Val Ser Gly Gly Tyr Pro Gln Cys Ala Pro
        115                 120                 125

Ala Val Tyr Ser Gly Asn Leu Ser Ser Pro Met Val Gln His His His
    130                 135                 140

His His Gln Gly Tyr Ala Gly Gly Ala Val Gly Ser Pro Gln Tyr Ile
145                 150                 155                 160

His His Ser Tyr Gly Gln Glu His Gln Ser Leu Ala Leu Ala Thr Tyr
                165                 170                 175
```

```
Asn Asn Ser Leu Ser Pro Leu His Ala Ser His Gln Glu Ala Cys Arg
            180                 185                 190

Ser Pro Ala Ser Glu Thr Ser Ser Pro Ala Gln Thr Phe Asp Trp Met
        195                 200                 205

Lys Val Lys Arg Asn Pro Pro Lys Thr Gly Lys Val Gly Glu Tyr Gly
    210                 215                 220

Tyr Leu Gly Gln Pro Asn Ala Val Arg Thr Asn Phe Thr Thr Lys Gln
225                 230                 235                 240

Leu Thr Glu Leu Glu Lys Glu Phe His Phe Asn Lys Tyr Leu Thr Arg
                245                 250                 255

Ala Arg Arg Val Glu Ile Ala Ala Ser Leu Gln Leu Asn Glu Thr Gln
            260                 265                 270

Val Lys Ile Trp Phe Gln Asn Arg Arg Met Lys Gln Lys Lys Arg Glu
        275                 280                 285

Lys Glu Gly Leu Leu Pro Ile Ser Pro Ala Thr Pro Pro Gly Asn Asp
    290                 295                 300

Glu Lys Ala Glu Glu Ser Ser Glu Lys Ser Ser Ser Ser Pro Cys Val
305                 310                 315                 320

Pro Ser Pro Gly Ser Ser Thr Ser Asp Thr Leu Thr Thr Ser His
                325                 330                 335
```

(2) INFORMATION FOR SEQ ID NO:5:

(i) SEQUENCE CHARACTERISTICS:
        (A) LENGTH: 1021 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
TGACGCATGG ACTATAATAG GATGAACTCC TTCTTAGAGT ACCCACTCTG TAACCGGGGA      60
CCCAGCGCCT ACAGCGCCCA CAGCGCCCCA ACCTCCTTTC CCCCAAGCTC GGCTCAGGCG     120
GTTGACAGCT ATGCAAGCGA GGGCCGCTAC GGTGGGGGGC TGTCCAGCCC TGCGTTTCAG     180
CAGAACTCCG GCTATCCCGC CCAGCAGCCG CCTTCGACCC TGGGGGTGCC CTTCCCCAGC     240
TCCGCGCCCT CGGGGTATGC TCCTGCCGCC TGCAGCCCCA GCTACGGGCC TTCTCAGTAC     300
TACCCTCTGG GTCAATCAGA AGGAGACGGA GGCTATTTTC ATCCCTCGAG CTACGGGGCC     360
CAGCTAGGGG GCTTGTCCGA TGGCTACGGA GCAGGTGGAG CCGGTCCGGG GCCATATCCT     420
CCGCAGCATC CCCCTTATGG GAACGAGCAG ACCGCGAGCT TTGCACCGGC CTATGCTGAT     480
CTCCTCTCCG AGGACAAGGA AACACCCTGC CCTTCAGAAC CTAACACCCC CACGGCCCGG     540
ACCTTCGACT GGATGAAGGT TAAGAGAAAC CCACCCAAGA CAGCGAAGGT GTCAGAGCCA     600
GGCCTGGGCT CGCCCAGTGG CCTCCGCACC AACTTCACCA CAAGGCAGCT GACAGAACTG     660
GAAAAGGAGT TCCATTTCAA CAAGTACCTG AGCCGGGCCC GGAGGGTGGA GATTGCCGCC     720
ACCCTGGAGC TCAATGAAAC ACAGGTCAAG ATTTGGTTCC AGAACCGACG AATGAAGCAG     780
AAGAAGCGCG AGCGAGAGGG AGGTCGGGTC CCCCCAGCCC CACCAGGCTG CCCCAAGGAG     840
GCAGCTGGAG ATGCCTCAGA CCAGTCGACA TGCACCTCCC GGAAGCCTC ACCCAGCTCT     900
GTCACCTCCT GAACTGAACC TAGCCACCAA TGGGGCTTCC AGGCACTGGA GCGCCCCAGT     960
CCAGCCCTAT CCCAGGCTCT CCCAACCCAG GCCTGGCTTC ACTGCCTGGG ATCTCTAGGC    1020
T                                                                    1021
```

(2) INFORMATION FOR SEQ ID NO:6:

(i) SEQUENCE CHARACTERISTICS:
        (A) LENGTH: 301 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Met Asp Tyr Asn Arg Met Asn Ser Phe Leu Glu Tyr Pro Leu Cys Asn
 1               5                  10                  15

Arg Gly Pro Ser Ala Tyr Ser Ala His Ser Ala Pro Thr Ser Phe Pro
            20                  25                  30

Pro Ser Ser Ala Gln Ala Val Asp Ser Tyr Ala Ser Glu Gly Arg Tyr
            35                  40                  45

Gly Gly Gly Leu Ser Ser Pro Ala Phe Gln Gln Asn Ser Gly Tyr Pro
 50                  55                  60

Ala Gln Gln Pro Pro Ser Thr Leu Gly Val Pro Phe Pro Ser Ser Ala
65                  70                  75                  80

Pro Ser Gly Tyr Ala Pro Ala Ala Cys Ser Pro Ser Tyr Gly Pro Ser
                85                  90                  95

Gln Tyr Tyr Pro Leu Gly Gln Ser Glu Gly Asp Gly Gly Tyr Phe His
            100                 105                 110

Pro Ser Ser Tyr Gly Ala Gln Leu Gly Gly Leu Ser Asp Gly Tyr Gly
            115                 120                 125

Ala Gly Gly Ala Gly Pro Gly Pro Tyr Pro Pro Gln His Pro Pro Tyr
130                 135                 140

Gly Asn Glu Gln Thr Ala Ser Phe Ala Pro Ala Tyr Ala Asp Leu Leu
145                 150                 155                 160

Ser Glu Asp Lys Glu Thr Pro Cys Pro Ser Glu Pro Asn Thr Pro Thr
                165                 170                 175

Ala Arg Thr Phe Asp Trp Met Lys Val Lys Arg Asn Pro Pro Lys Thr
            180                 185                 190

Ala Lys Val Ser Glu Pro Gly Leu Gly Ser Pro Ser Gly Leu Arg Thr
            195                 200                 205

Asn Phe Thr Thr Arg Gln Leu Thr Glu Leu Glu Lys Glu Phe His Phe
210                 215                 220

Asn Lys Tyr Leu Ser Arg Ala Arg Arg Val Glu Ile Ala Ala Thr Leu
225                 230                 235                 240

Glu Leu Asn Glu Thr Gln Val Lys Ile Trp Phe Gln Asn Arg Arg Met
                245                 250                 255

Lys Gln Lys Lys Arg Glu Arg Glu Gly Gly Arg Val Pro Pro Ala Pro
            260                 265                 270

Pro Gly Cys Pro Lys Glu Ala Ala Gly Asp Ala Ser Asp Gln Ser Thr
            275                 280                 285

Cys Thr Ser Pro Glu Ala Ser Pro Ser Ser Val Thr Ser
290                 295                 300
```

(2) INFORMATION FOR SEQ ID NO:7:

(i) SEQUENCE CHARACTERISTICS:
        (A) LENGTH: 1030 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
TGACGCATGG ACTATAATAG GATGAACTCC TTCTTAGAGT ACCCACTCTG TAACCGGGGA      60
CCCAGCGCCT ACAGCGCCCA CAGCGCCCAC AGCGCCCCAA CCTCCTTTCC CCCAAGCTCG     120
GCTCAGGCGG TTGACAGCTA TGCAAGCGAG GGCCGCTACG GTGGGGGGCT GTCCAGCCCT     180
GCGTTTCAGC AGAACTCCGG CTATCCCGCC CAGCAGCCGC CTTCGACCCT GGGGGTGCCC     240
TTCCCCAGCT CCGCGCCCTC GGGGTATGCT CCTGCCGCCT GCAGCCCAG CTACGGGCCT      300
TCTCAGTACT ACCCTCTGGG TCAATCAGAA GGAGACGGAG GCTATTTTCA TCCCTCGAGC     360
TACGGGGCCC AGCTAGGGGG CTTGTCCGAT GGCTACGGAG CAGGTGGAGC CGGTCCGGGG     420
CCATATCCTC CGCAGCATCC CCCTTATGGG AACGAGCAGA CCGCGAGCTT TGCACCGGCC     480
TATGCTGATC TCCTCTCCGA GGACAAGGAA ACACCCTGCC CTTCAGAACC TAACACCCCC     540
ACGGCCCGGA CCTTCGACTG GATGAAGGTT AAGAGAAACC CACCCAAGAC AGCGAAGGTG     600
TCAGAGCCAG GCCTGGGCTC GCCCAGTGGC CTCCGCACCA ACTTCACCAC AAGGCAGCTG     660
ACAGAACTGG AAAAGGAGTT CCATTTCAAC AAGTACCTGA GCCGGGCCCG GAGGGTGGAG     720
ATTGCCGCCA CCCTGGAGCT CAATGAAACA CAGGTCAAGA TTTGGTTCCA GAACCGACGA     780
ATGAAGCAGA AGAAGCGCGA GCGAGAGGGA GGTCGGGTCC CCCCAGCCCC ACCAGGCTGC     840
CCCAAGGAGG CAGCTGGAGA TGCCTCAGAC CAGTCGACAT GCACCTCCCC GGAAGCCTCA     900
CCCAGCTCTG TCACCTCCTG AACTGAACCT AGCCACCAAT GGGGCTTCCA GGCACTGGAG     960
CGCCCCAGTC CAGCCCTATC CCAGGCTCTC CCAACCCAGG CCTGGCTTCA CTGCCTGGGA    1020
TCTCTAGGCT                                                           1030
```

(2) INFORMATION FOR SEQ ID NO:8:

(i) SEQUENCE CHARACTERISTICS:
        (A) LENGTH: 304 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Met Asp Tyr Asn Arg Met Asn Ser Phe Leu Glu Tyr Pro Leu Cys Asn
 1               5                  10                  15

Arg Gly Pro Ser Ala Tyr Ser Ala His Ser Ala His Ser Ala Pro Thr
            20                  25                  30

Ser Phe Pro Pro Ser Ser Ala Gln Ala Val Asp Ser Tyr Ala Ser Glu
        35                  40                  45

Gly Arg Tyr Gly Gly Gly Leu Ser Ser Pro Ala Phe Gln Gln Asn Ser
    50                  55                  60

Gly Tyr Pro Ala Gln Gln Pro Pro Ser Thr Leu Gly Val Pro Phe Pro
65                  70                  75                  80

Ser Ser Ala Pro Ser Gly Tyr Ala Pro Ala Ala Cys Ser Pro Ser Tyr
                85                  90                  95

Gly Pro Ser Gln Tyr Tyr Pro Leu Gly Gln Ser Glu Gly Asp Gly Gly
           100                 105                 110

Tyr Phe His Pro Ser Ser Tyr Gly Ala Gln Leu Gly Gly Leu Ser Asp
       115                 120                 125

Gly Tyr Gly Ala Gly Gly Ala Gly Pro Gly Pro Tyr Pro Pro Gln His
```

```
                    130                 135                 140
Pro Pro Tyr Gly Asn Glu Gln Thr Ala Ser Phe Ala Pro Ala Tyr Ala
145                 150                 155                 160

Asp Leu Leu Ser Glu Asp Lys Glu Thr Pro Cys Pro Ser Glu Pro Asn
                    165                 170                 175

Thr Pro Thr Ala Arg Thr Phe Asp Trp Met Lys Val Lys Arg Asn Pro
                180                     185                 190

Pro Lys Thr Ala Lys Val Ser Glu Pro Gly Leu Gly Ser Pro Ser Gly
                195                 200                 205

Leu Arg Thr Asn Phe Thr Thr Arg Gln Leu Thr Glu Leu Glu Lys Glu
    210                 215                 220

Phe His Phe Asn Lys Tyr Leu Ser Arg Ala Arg Arg Val Glu Ile Ala
225                 230                     235                 240

Ala Thr Leu Glu Leu Asn Glu Thr Gln Val Lys Ile Trp Phe Gln Asn
                245                 250                     255

Arg Arg Met Lys Gln Lys Lys Arg Glu Arg Glu Gly Gly Arg Val Pro
                260                 265                 270

Pro Ala Pro Pro Gly Cys Pro Lys Glu Ala Ala Gly Asp Ala Ser Asp
            275                 280                 285

Gln Ser Thr Cys Thr Ser Pro Glu Ala Ser Pro Ser Ser Val Thr Ser
290                 295                 300
```

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

GCATGGACTA TAATAGGATG    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

TCTTGGGTGG GTTTCTCTTA    20